United States Patent [19]

Barberá-Guillem et al.

[11] Patent Number: 5,536,642
[45] Date of Patent: Jul. 16, 1996

[54] DIAGNOSTIC AND PROGNOSTIC METHODS FOR SOLID NON-LYMPHOID TUMORS AND THEIR METASTASES

[76] Inventors: Emilio Barberá-Guillem, Apt. 209B Chestnut Ridge, Amherst, N.Y. 14228; Stefan A. Cohen, 24 Wagon Wheel Dr., East Amherst, N.Y. 14051

[21] Appl. No.: 118,969

[22] Filed: Sep. 9, 1993

[51] Int. Cl.$^6$ .......................... G01N 33/53; G01N 33/574
[52] U.S. Cl. .............. 435/7.23; 435/7.9; 435/6; 436/64; 436/813
[58] Field of Search ............... 435/7.23, 6, 7.9; 424/85.2; 436/64, 813

[56] References Cited

U.S. PATENT DOCUMENTS

| | | | |
|---|---|---|---|
| 4,690,915 | 9/1987 | Rosenberg | 514/2 |
| 4,789,658 | 12/1988 | Yoshimoto et al. | 514/12 |
| 4,939,093 | 7/1990 | McGrogan et al. | 435/252.3 |
| 5,006,459 | 4/1991 | Kung et al. | 435/5 |
| 5,061,488 | 10/1991 | Wiltrout et al. | 424/85.2 |
| 5,089,261 | 2/1992 | Nitecki et al. | 424/85.2 |
| 5,089,702 | 3/1992 | Zimmerman et al. | 424/85.21 |
| 5,126,129 | 6/1992 | Wiltrout et al. | 424/85.2 |
| 5,229,109 | 7/1993 | Grimm et al. | 424/85.2 |

OTHER PUBLICATIONS

Barberá–Guillem et al., "Differences in the Lectin–binding patterns of the Periportal and Perivenous Endothelial Domains in the Liver Sinusoids" Journal of Hepatology, vol. 14, No. 1, 1991, pp. 131–139.

Barberá–Guillem et al., "Selective Implantation and Growth in Rats and Mice of Experimental Liver Metastasis in Acinar Zone One" Cancer Research, vol. 49, Jul. 15, 1989, pp. 4003–4010.

Yasumura, S., et al., Proc. Annu. Meet. Am. Assoc. Cancer Res., vol. 33: A 290, 1992.

*Primary Examiner*—Toni R. Scheiner
*Attorney, Agent, or Firm*—Hodgson, Russ, Andrews, Woods & Goodyear

[57] ABSTRACT

The present invention is directed to the measurement of cell-associated interleukin-2 receptor α (IL-2Rα) expression in solid non-lymphoid tumors, and the use of such measurement In prognosing the metastatic potential of the tumor, diagnosing the metastatic localization of non-lymphoid tumor, and aiding the monitoring of efficacy of anticancer therapy against metastatic cells of non-lymphoid tumor. The present invention also relates to the use of T-cell receptor (tumor specific TCRβ idiotype) in monitoring the efficacy of anticancer therapy against non-lymphoid tumors.

11 Claims, 5 Drawing Sheets

DIAGNOSTIC AND PROGNOSTIC METHODS FOR SOLID NON-LYMPHOID TUMORS AND THEIR METASTASES

FIELD OF THE INVENTION

The present invention relates to a novel methods involving the correlation between the probability of metastasis (metastatic potential) of non-lymphoid tumors with the expression of Interleukin-2 receptor alpha (IL-2Rα), wherein the measurement of IL-2Rα expressed by the tumor cells can be used to establish a metastasis prognosis; aid in diagnosis of metastases localization; target therapeutic treatment in prometastatic territories, and monitor efficacy of therapeutic treatment of tumors, particularly metastatic tumor cells, or tumor cells having a high probability of metastasis. The present invention also relates to the expression by solid non-lymphoid tumors of T-cell receptor β chain (TCRβ), or tumoral specific variants thereof, and methods for targeting therapeutic treatment, and monitoring efficacy of therapeutic treatment of these tumors.

BACKGROUND OF THE INVENTION

1. Metastasis

Metastasis is the spread of malignant tumors to secondary sites remote from the original or primary tumor. Metastasis presents a cancer clinician with difficulty in diagnosing and treating the malignant tumor because (a) metastases may be comprised of as little as one or a few cells thereby evading clinical diagnosis even with modern techniques; (b) often metastases have already been seeded by the time a patient is diagnosed with a malignant non-lymphoid tumor (Silverberg et al., 1989, *CA Cancer J. Clin.* 39:3–21); (c) treatment is more complex than simple surgical excision of the primary tumor; (d) systemic therapy for metatstatic non-lymphoid tumors, such as renal cell carcinoma (Rosenberg et al., 1985, *N. Engl. J. Med.* 313:1485–1492), remains ineffective with little survival advantage; and (e) not all malignant tumors have the same metastatic potential and no direct relationship has been established in determining whether any particular nonolymphoid tumor will develop metastasis.

2. T-Cell Surface Molecules, Interleukin-2, and the IL-2 Receptor.

Monoclonal antibodies have been used to characterize and classify T cell surface molecules such as the clusters of differentiation (CD) of human leukocyte antigens. The T cell receptor (TCR) is an integral membrane protein, expressed on the surface of T lymphocytes, occuring as a disulfide linked heterodimer which is non-covalently associated with CD3. TCR has been linked to autoimmune disease as anti-TCR antibodies have shown therapeutic potential for treating autoimmune disease (Basi et al., 1992, *J. Immunol. Methods* 155:175–191). Of the T cell surface molecules, a correlation between an increase in concentration of soluble CD8 in the serum of children with non-Hodgkins lymphoma is disclosed by Kung et al. (U.S. Pat. No. 5,006,459). The elevated levels of CD8 appear related to the stage of the lymphoma and responsiveness to therapy.

IL-2 and the IL-2 receptor (IL-2R) interact in regulating the T cell immune response. The IL-2R is present in three forms classified by their binding affinity for IL-2 and by the different combinations of two binding proteins (the α and β chains). High affinity IL-2R contain both α and β chains, intermediate affinity contain β chains, and low affinity contain α chains (Leonard et al., 1990, *Prog. Clin. Biol. Res.*, 352:179–187). IL-2Rα is only expressed on activated T cells, and it has been shown that IL-2 exerts its T cell growth promoting effects via stimulation of the α chain. Kung et al. (supra) disclose the elevation of serum IL-2 receptors (IL2R) in patients with active lymphatic cancers such as leukemia and lymphoma; and further, the concentration of soluble ILR2 bears a direct relationship with the severity and prognosis of the lymphatic cancer. They also disclose that soluble ILR2 receptors were generally not elevated in patients with non-lymphatic cancers. In addition, the level of soluble ILR2 correlated poorly with the number of circulating IL-2R bearing lymphocytes.

Immunotherapy with lymphokines are being used as a systemic form of anticancer therapy in attempting to stimulate the host immune response against tumor cells. Different compositions comprising IL-2 have been described including: U.S. Pat. No. 5,229,109 to Grimm et al. disclosing low toxity IL-2 analogues; U.S. Pat. No. 5,089,261 to Nitecki et al., disclosing IL-2 conjugated to a polymer to reduce immunogenicity and to enhance solubility and circulating half-life; U.S. Pat. Nos. 5,061,488 and 5,126,129 to Wiltrout et al., describing compositions and methods involving a combination of flavone-8-acetic acid and recombinant IL-2; U.S. Patent No. 5,098,702 to Zimmerman et al. disclosing a combination of IL-2 and/or Interferon-β and tumor necrosis factor against tumor cells; U.S. Pat. No. 4,939,093 to McGrogan et al. disclosing methods for the production of human IL-2-like polypeptides; and U.S. Pat. No. 4,789,658 to Yoshimoto et al., disclosing the production of human IL-2 and its use against diseases including neoplasms. U.S. Pat. No. 4,690,915 to Rosenberg discloses adoptive immunotherapy involving treating a patient with immune cells, lymphokine activated lymphocytes, with IL-2 immunotherapy.

Thus, the background and related art does not disclose or correlate the existence of IL-2Rα with metastases or the metastatic potential of solid, nonolymphoid tumors. Further, no known methods exist for utilizing the presence of IL-2Rα in establishing the prognosis of the metastatic potential of non-lymphoid tumors; or in the diagnosis of or targeting anticancer agents to their metastases. Nor does the background and related art disclose methods for administering anticancer therapy against non-lymphoid metastatic cells directly to the areas in organs where metastases develop (prometastatic territories), rather than conventional systemic administration. Additionally, it has not disclosed that TCRβ is expressed on non-lymphoid tumors and that TCRβ represents a target for methods of anticancer therapy directed against tumors expressing TCRβ. The methods of the present invention will greatly facilitate the diagnosis and anticancer therapy of individuals bearing non-lymphoid tumors, metastases thereof, or non-lymphoid tumors having a high probability of metastasis.

SUMMARY OF THE INVENTION

A primary object of the invention is to provide a method for determining the metastatic potential of a non-lymphoid tumor by determining the tumor cell-associated expression of IL-2Rα.

Another object of the invention is to provide methods for targeting anticancer agents to non-lymphoid tumors, metastases thereof, or non-lymphoid tumors having a high probability of metastasis. A related object of the present invention is to provide methods and compounds for targeting anticancer therapy against metastatic cells to the prometastatic territories of the affected organ(s).

A further object of the present invention is to provide a method for monitoring the effectiveness of anticancer therapy against non-lymphoid tumors, metastases thereof, or tumors having a high probability of metastasis.

BRIEF DESCRIPTION OF THE FIGURES

FIG. 5A is a plot of B16F10 cell proliferation versus concentration of Il-2.

FIG. 5B is a plot of CTLL-2 cell proliferation versus concentration of IL-2.

DETAILED DESCRIPTION OF THE INVENTION

The present invention is directed to the measurement of TCRβ, or tumoral-specific variants thereof, and/or IL-2Rα expressed by non-lymphoid tumor cells. The measurement of IL-2Rα can be used to aid in the diagnosis of metastases and to determine the metastatic potential of solid, non-lymphoid tumors. The measurement of IL-2Rα or TCRβ can be used in targeting anticancer agents to non-lymphoid tumors expressing the respective receptor; and in monitoring the efficacy of anticancer therapy of such tumors expressing that receptor. This present invention consists of the proceeding elements gathered in three clusters:

1. Methods for prognosis of metastasis probability and metastases localization.

2. Treatment with anticancer therapy localizing to prometastatic territories, comprising targeted compounds directed to metastatic colonies forming cells and to dormant metastatic tumor cells, and monitoring the effect of that treatment.

3. Treatment with anticancer therapy directed to non-lymphoid tumor cells expressing TCRβ, or tumoral-specific β chain variants.

1. Method for prognosis of metastasis probability (metastatic potential) and diagnosing metastases localization.

1.1 The relation between IL-2Rα expression and metastasis probability.

The present invention provides methods for measuring IL-2Rα expressed by solid, non-lymphoid tumors. In one embodiment of the present invention, the cell-associated expression of IL-2Rα is measured on/in solid, non-lymphoid tumors. The experiments showed that human and experimental metastatic cells on non-lymphoid tumors express IL-2Rα in relation to their metastatic potential. Also, the number of metastases obtained are directly proportional to the percent of tumor cells expressing IL-2Rα. The following examples in Sections A through E demonstrate the detection of cell-associated IL-2Rα in human and experimental tumors using one or more methods selected from the group consisting of fluorescence microscopy (measuring surface IL-2Rα), Western blot analysis (measuring internal and membrane IL-2Rα fractions), mRNA Northern and slot blot analysis (measuring IL-2Rα m-RNA expression), enzymatic amplification and analysis of mRNA (measuring IL-2Rα m-RNA expression), and fluorescence activated cell sorting (FACS, measuring surface IL-2Rα) analysis. The human and experimental tumors were obtained as follows: B16F10 melanoma cells were supplied by Dr. MF Poupon (Paris). Colon 51B and colon 51B lim 10 cells were supplied by Dr. R. Bresalier (USA). MCA-26 cells were supplied by Dr. I. Fidler (USA). MMC-7489 and cells were supplied by Dr. J. Vaageand (USA). SW480, SW480E, SW480R and SW620 were supplied by Dr. I. B. Weinstein. Human biopsies were supplied by Dr. Alonso and Dr. Pellin (Spain). All tumor cell lines were grown in plastic T-flasks in a humid atmosphere of 5% $CO_2$ in air, in adequate media supplemented with 10% FBS and containing penicillin and streptomycin.

A. Fluorescence microscopy of IL-2Rα

Tumor biopsies or surgical specimens containing non-lymphoid tumor may be disaggregated, and prepared directly for fluorescence analysis. Alternately, the tumor cells can be cultured in 8-well slide plates (Biotek) for 48 hours, then the supernatants removed and the wells washed gently with PBS and fixed in Carnoy's fixative. After three PBS rinses, the cells were incubated for 30 minutes at 37° C. in a solution of PBS containing 4 μl/ml FITC-rat anti-mouse-IL-2Rα $IgG_2$ monoclonal antibody (clone AMT, Boehringer Manheim). After incubation, the wells were washed twice with PBS. Controls were prepared only with FITC rat anti-mouse-$IgG_2$ monoclonal antibody (Boehringer Manheim). The cells were observed with a laser-scanning fluorescence microscope.

B. Western-blot for IL-2Rα For Western-blot analysis $5 \times 10^6$ tumor cells, and control cells (ConA-activated spleen cells and CTLL-2 cells) were collected into PBS containing 1 mM PMSF. After washing, cells were homogenized in ice using 50 strokes of a Dounce homogenizer in buffer 10 mM Tris-ClH pH 7.4, containing 0.25 M sucrose, 1 mM $MgCl_2$, 5 mM $CaCl_2$ and a mixture of protease inhibitors. After pelleting nuclei (at 600×g for 10 minutes), the post-nuclear supernatant was centrifuged at 100,000×g for 1 hour to generate a cytosol fraction and a crude membrane fraction. Polyacrylamide gel electrophoresis was performed. The protein was transferred onto nitrocellulose filters by electrophoretic transfer for 2 hours at 40 V. The filter was then incubated in avidin D blocking solution with 3% normal serum, following three washes with TTBS. The monoclonal antibody anti-mouse interleukin-2 receptor was added at a 1:40 dilution in TTBS and incubated for 2 hours. After three washes, a biotinylated rabbit-anti rat Ig G was added at a 1:200 dilution in TTBS for 1 hour. Following three washes with TTBS, the blot was incubated with avidin DH and biotinylated horseradish peroxidase H for 30 minutes. The blot was then incubated with DAB and the sites of antibody binding were revealed by brown precipitate. The molecular weight (MW) marker proteins were: beta-galactosidase (116 Kd), Bovine albumin (66 Kd), Egg albumin (45 Kd) and carbonic anhydrase (29 Kd).

The physical presence of cell-associated IL-2Rα, expressed by non-lymphoid cells, may also be determined from the membrane fraction or cytosolic extract of such cells in assays which utilize IL-2Rα as an antigen. Such assays includes any immunoassay system known in the art including, but not limited to, radioimmunoassays, enzyme-linked immunosorbent assays (ELISA), "sandwich" assays, precipitin reactions, agglutination assays, and fluorescent immunoassays.

C. mRNA Northern and slot-blot analysis mRNA was obtained from spleen cells, ConA-activated spleen cells, and tumor cells. Tumor cells were examined as untreated, and as pretreated in vitro. Pretreatments of tumor cells was accomplished by incubating the cells for 24 hours either in regular media containing 125 U/ml IL-2 in 5% $CO_2$, in media containing 10 U/ml IL-1β, or in media containing 5 μg/ml ConA. Cells were detached by brief exposure to 0.1% trypsin plus 2mM EDTA, then incubated for 48 h. in spinner-flasks in DMEM plus 10% FBS at 5% $CO_2$.

After extraction and quantification of the mRNA (shown to be intact by 0.7% agarose gel electrophoresis), a total of 20 μg of purified RNA was separated on a 1.2% agarose gel containing 2.2 M formaldehyde. The electrophoresis was performed at 80 V. The tracks containing the molecular size standard was cut off the gels and the migration distances were measured. The gels were rinsed and transferred onto nitrocellulose filter. Or alternatively, samples of RNA were blotted on nitrocellulose filter presoaked in 10×SSC with a slot blot apparatus. Two μg of mRNA were diluted in a final volume of 100 μl in 10×SSC-formaldehyde and denatured by heating at 65° C. for 10 minutes before blotting. mRNA was cross-linked to the nitrocellulose filter with UV irradiation. The blots were prehybridized 4 hours at 45° C. in 6×SSC, 0.5 SDS, 5×Denhardt's, 10 mM EDTA, 50 μg/ml of sheared salmon sperm DNA, and 50 μg/ml of E. coli tRNA. Simultaneously 5 picomoles of DNA probe, to murine or human IL-2Rα and IL-2 (Amgen Biologicals), were labeled according to standard protocol by 5=end-labeling of oligonucleotide probe with gamma-$^{32}$P ATP. 100 μg of human beta-actin DNA probe (Clontech) was labeled by random priming. The radiolabeled probes ($2\times10^9$ cpm/μl specific radioactivity) were used for hybridization of mRNA blot at 45° C. for 24 hours. Then the blots were washed with 5×SSC-0.1 SDS at the hybridization temperature for 20 minutes. The blots were exposed to x-ray film with intensifying screens at −70° C. for various periods. The probes were removed from the filters by incubation in sterile water at 100° C. for 10 minutes and the filters were rehybridized with other probes. Quantitative analysis of 10 autoradiograms were performed with video-densitometry.

D. Enzymatic amplification of tumor cell mRNA

Expression of IL-2Rα mRNA can be detected by extracting and purifying mRNA from nonolymphoid tumor cells and then subjecting the purified mRNA to enzymatic amplification to obtain sufficient quantities for analysis and detection. Enzymatic amplification techniques which could be employed include those known in the art such as PCR™ (polymerase chain reaction), QB replicase, and NASBA (nucleic acid sequence-based amplification). Detection of the amplified nucleic acid includes techniques known in the art including, but not limited to, agarose gel electrophoresis and Northern blotting; fluorescence-based hybridization assays; chemiluminescence-based hybridization assays, and capture hybridization microtiter assays. Oligonucleotides primers and probes can be synthesized from the nucleic acid sequence of the IL-2Rα gene (Leonard et al., 1984, Nature 311:626–631). Probes can be synthesized with methods known to those skilled in the art to incorporate either non-isotopic or isotopic label. Alternatively, the label may be incorporated directly into the amplified product.

In this example, single-stranded cDNA, obtained by reverse transcription from the extracted tumor cell mRNA, was amplified by PCR™ utilizing primers for IL-2R and Il-2Rα genes from commercial sources. The amplified products were separated on a 1.2% agarose gels and stained with ethidium bromide in parallel with positive and negative controls. Quantification was made with Photoquant System™ (BAF, Spain).

E. FACS analysis

Tumor cells were cultured in 24-wells plates for 48 hours, and then the supernatants were removed and the wells washed gently with PBS, then the cells were gently scraped from tissue culture plates and incubated in a solution of PBS containing 1 μg/ml rat anti-mouse-IL-2Rα monoclonal antibody for 30 minutes at 4° C. After being washed, the cells were incubated for 30 minutes at 4° C. in a solution of PBS containing 20 μg/ml FITC-rabbit anti-rat Ig antibody, fixed with 1% paraformaldehyde, and analyzed within 48 hours using a FACS (Coulter). In all cases, controls were prepared with second antibody alone. Spleen cells were used as negative control and ConA-activated spleen cells as positive control of antigen expression. Quantitative analysis of IL-2Rα expression on tumor cells was performed using a fluorescence activated cell sorter.

Table 1 contains human and experimental non-lymphoid tumors in which the metastatic potential was compared with their cell-associated IL-2Rα expression. The in vivo metastatic potential of the human tumors was determined by clinical observation. The metastatic potential of the experimental tumors was determined by in vivo tumor cell growth and metastasis efficiency analysis (described below in 1.1, Section F).

Table 1 shows that cell-associated expression of IL-2Rα correlates well with the metastatic potential of experimental and human non-lymphoid tumors, where the metastic potential has been determined.

TABLE 1

IL-2Rα Expression and Metastatic Potential of Non-Lymphoid Tumor Cells

| Tumor | Description | Metastatic Potential | mRNA IL-2Rα | Surface IL-2Rα | Internal IL-2Rα |
|---|---|---|---|---|---|
| Mouse Tumors | | | | | |
| 3LL p100 | Lewis Lung Carcinoma | Low | None | — | None |
| MMC4908 | Mammary Carcinoma | Low | ND | — | 10%* |

TABLE 1-continued

IL-2Rα Expression and Metastatic Potential of
Non-Lymphoid Tumor Cells

| Tumor | Description | Metastatic Potential | mRNA IL-2Rα | Surface IL-2Rα | Internal IL-2Rα |
|---|---|---|---|---|---|
| MMC7849 | Mammary Carcinoma | High | ND | + | 100%* |
| MCA26 | Colon Carcinoma | High | ND | + | 100%* |
| MCA38 | Colon Carcinoma | Low | ND | − | 75%* |
| 51B | Colon Carcinoma | Low[1] | ND | − | 10%* |
| 51B-Lim10 | Colon Carcinoma | High[1] | ND | + | 100%* |
| B16F10 | Melanoma | High | High | + | 100%* |
| B16F10LM (B) | Liver met. microfoci Melanoma | Metastasis | ND | ND | 100%* |
| Human Tumors | | | | | |
| SW480E | Colon Carcinoma Prim. Tum. (CL) | Low[2] | Low | − | <1%* |
| SW480 | Colon Carcinoma Prim. Tum. (CL) | Low[2] | Low | + | 10%* |
| SW480R | Colon Carcinoma Prim. Tum. (CL) | High[2] | High | + | 100%* |
| SW620 | Colon Carcinoma Metast. (CL) | High[2] | High | + | 100%* |
| PC3 | Prostate Carcinoma (CL) | ND | ND | + | 75%* |
| MCF7 | Breast Carcinoma (CL) | ND | ND | − | 50%* |
| A549 | Lung Carcinoma (CL) | ND | ND | − | 50%* |
| HepG2 | Hepatoma (CL) | ND | ND | − | 75%* |
| LS174T | Colonic Carcinoma (CL) | ND | ND | − | 50%* |
| VA59P (B) | Osteo Sarcoma | Prim.Tum. | Low | ND | |
| VA59M (B) | Limph.N.Met. (VA59P) | Metastatis | High | ND | |
| BICO5P (B) | Colon Carcinoma | Prim.Tum. | ND | ND | 5%** |
| BIC52MH (B) | Liver Met.(BIO5P) | Metastasis | ND | ND | 75%** |
| BIM01MG (B) | Limph.N.Met. Melanoma | Metastasis | ND | ND | 75%** |
| BIM02MG (B) | Limph.N.Met. Melanoma | Metastasis | ND | ND | 75%** |

(CL) Cultured cell line (B) Tissue sample from the patient
*Percentage of tumor cells expressing IL-2Rα in very significant amounts (fluorescence intensity higher than 10× intensity of the negative control).
**Percentage of surface area of tumor tissue section covered by positive cells, measured by quantitative fluorescence microscopy.
[1]Bresalier et al., 1987, Cancer Research 47:1398–1406.
[2]Tomita et al., 1992, Cancer Research 52:6840–6847.

F. The number of metastases in relation to the percentage of tumor cells expressing cell-associated IL-2Rα

To illustrate this embodiment, B16F10 melanoma cells were treated under different conditions to contrast the number of metastatic loci with the intensity or percentage of metastatic cells expressing IL-2Rα. The in vitro pretreatments consisted of incubating, at 37° C. in 5%$CO_2$, a different group of cells in of the following solutions: A) for 24 hours in regular growth media (control); B) for 24 hours in media containing 125 U/ml IL-2 (activates growth of metastatic cells); C) for 24 hours in media containing 10 U/ml IL-1β (activates cell growth); D) 24 hours in media containing 5 μg/ml ConA (activates cell growth); or E) detaching the cells by brief exposure to 0.1% trypsin plus 2mM EDTA, then incubation of the cells for 48 hours in spinner flasks in DMEM plus 10% FBS (enhances cell growth).

After the in-vitro pretreatments, the supernatants were removed from someof the plates containing cells representative of each of the 5 groups; the cells were washed gently with PBS; adherent cells were gently scraped from the tissue culture plate; and the cells were incubated in a solution of PBS containing 1μg/ml rat anti-mouse IL-2Rα monoclonal antibody for 30 minutes at 4° C. After being washed, the cells were incubated for 30 minutes for at 4° C. in a solution of PBS containing 20 μg/ml FITC-rabbit anti-rat Ig antibody. The cells were then fixed with 1% paraformaldehyde and analyzed within 48 hours by FACS for quantitative analysis of IL-2Rα expression. For antigen expression, spleen cells were used as a negative control, and ConA-activated spleen cells as a positive control.

A total of $5 \times 10^5$ viable tumor cells, from each of the 5 different pretreatment groups, and in a volume of 0.05 ml, were injected into the upper pole of spleen of anesthetized mice. Cells from each different pretreatment were injected into a group of twenty mice. Five minutes later the animals were splenectomized. The groups of twenty animals were killed 7 days after tumor cell injection by cervical dislocation; their lungs and livers were removed and frozen in liquid nitrogen. 10 and 40 μm liver serial cryostat sections were cut at 200 μm gaps. These sections were stained for succinate-dehydrogenase (SDH-staining); immersed in acetone for 45 seconds at −20° C., and then rinsed twice for 5 minutes in PBS. Sections were examined with a microscope provided with image analysis facilities. Images were obtained from each field by transmitted light (SDH-staining). Individual foci were clearly delineated as non-SDH-staining regions of liver tissue. The frequency and volumes of individual foci and the total tumor volume, in each liver, were calculated from the image analysis data using specially modified software (DPLAN, Spain) according to described stereologic criteria (Aherne & Dunnill, Morphometry, ed. Edward Arnold, London, 1982).

Figure 1:
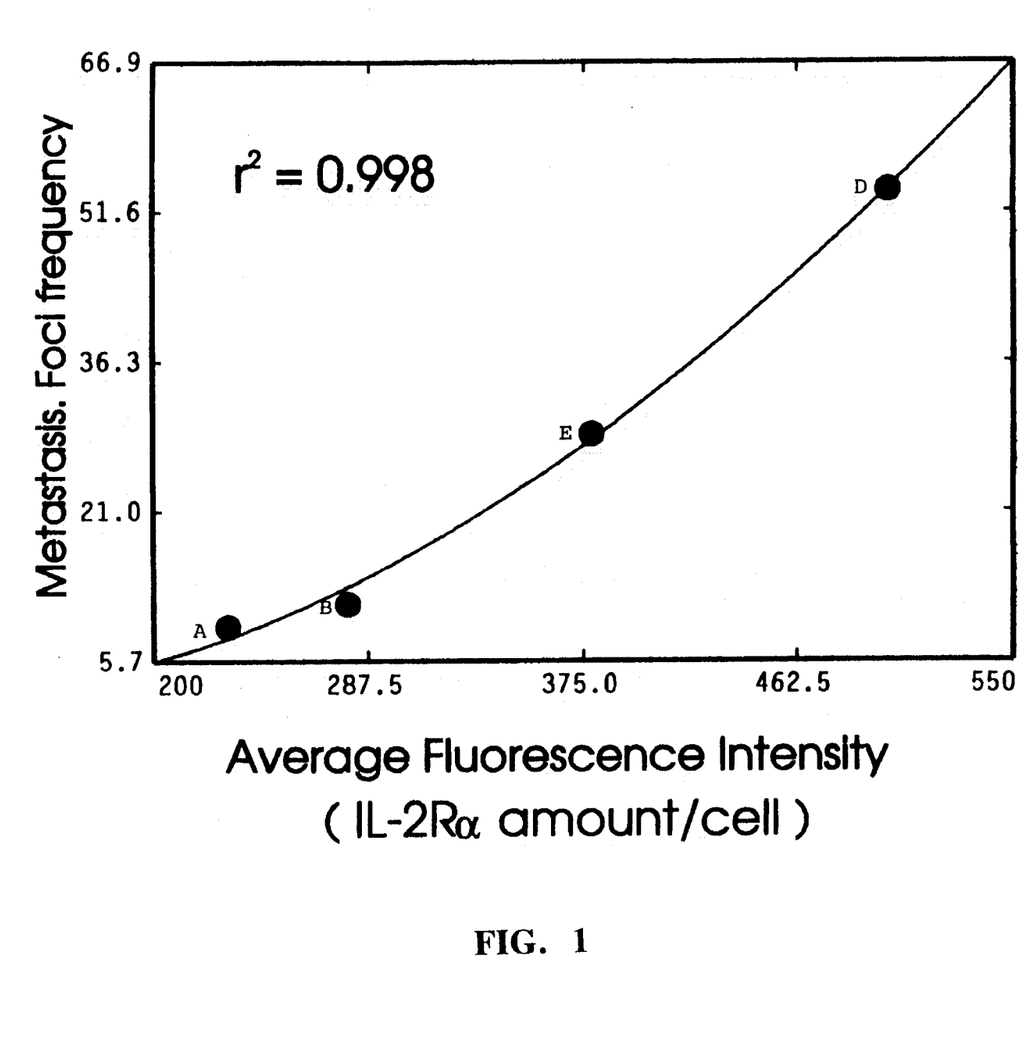
FIG. 1 is a graph showing a plot of metastatic foci frequency versus the average fluorescence intensity (IL-2Rα expression) per melanoma cell wherein the circles A,B,D, and E represent cells of different pretreatment groups, and the metastases of animals receiving cells of that respective group.
Figure 2:
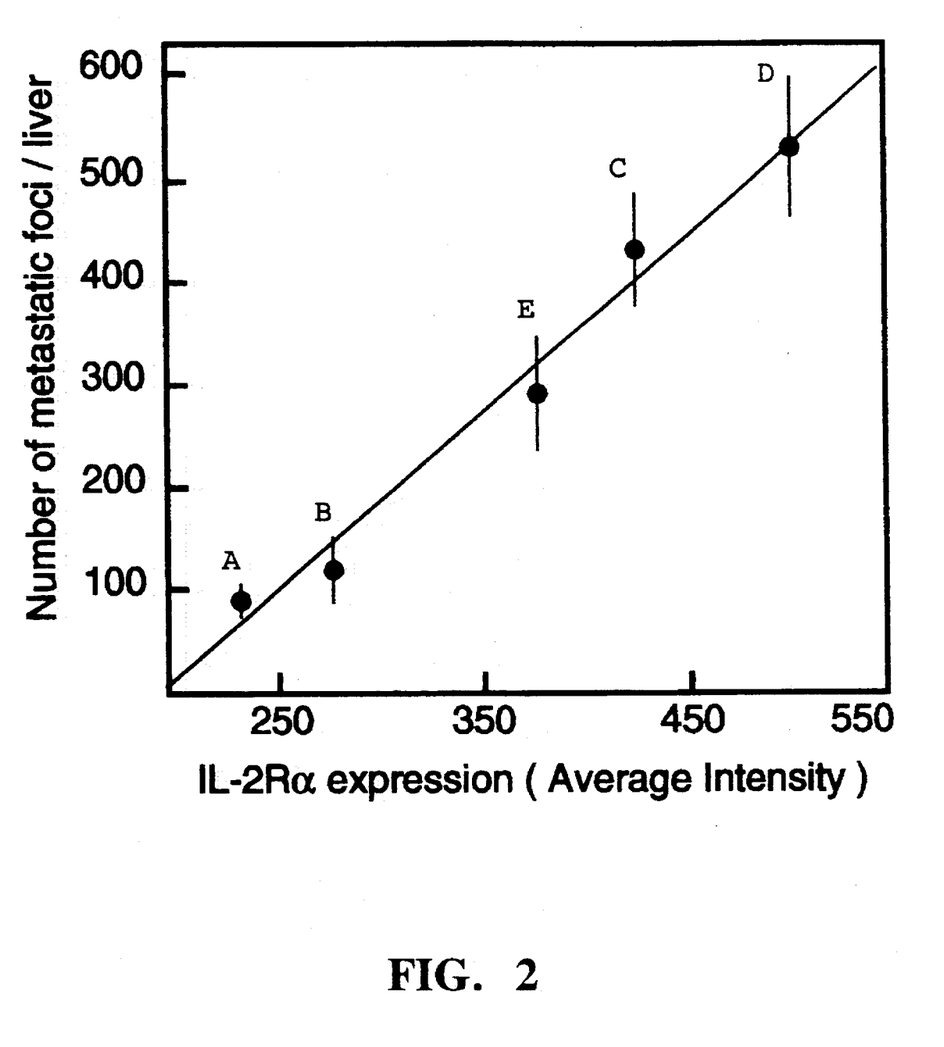
FIG. 2 is a graph showing a plot of the number of metastatic foci in the liver versus the average intensity of the whole sample (relating to expression of IL-2Rα), wherein the circles A–E represent cells of different pretreatment groups, and the metastases of animals receiving cells of that respective group.
Figure 3:
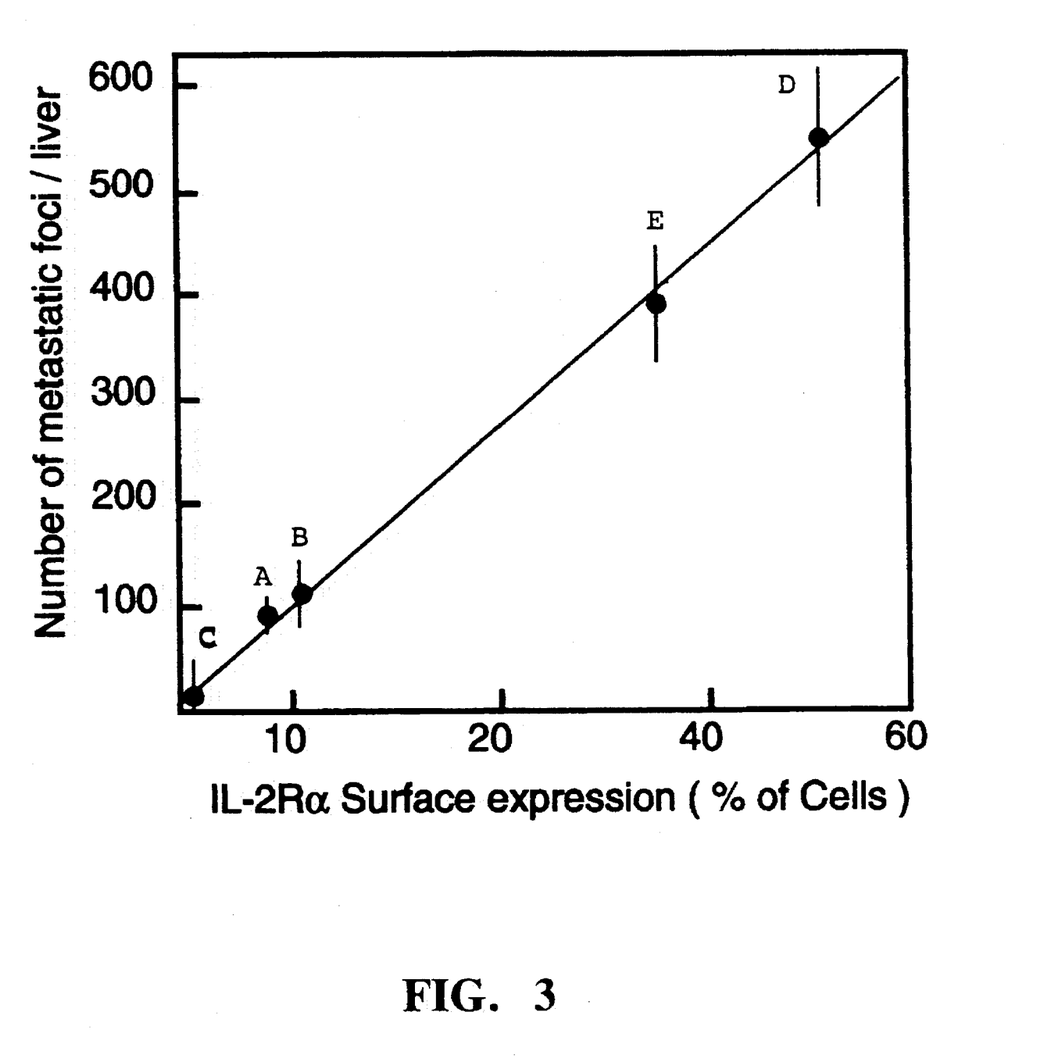
FIG. 3 is a graph showing a plot of the number of metastatic loci in the liver versus the percentage of cells expressing IL-2Rα, wherein the circles A–E represent cells of different pretreatment groups, and the metastases of animals receiving cells of that respective group.

The results are depicted in FIGS. 1 and 2. FIG. 1, showing the metastatic foci frequency plotted against the IL-2Rα amount expressed per cell (average of 10,000 cells) for cells from each different pretreatment group, indicates that an increase in IL-2Rα cell expression correlates with an increase in frequency of metastatic foci. For example, the greatest number of IL-2Rα receptors expressed per cell occured in those cells exposed to ConA. The ConA-activated melanoma cells were also the group of cells wherein the frequency of metastatic foci was found to be the greatest (FIG. 1, circle D). FIG. 2, showing the number of metastatic foci in the liver plotted against the IL-2Rα expression in the whole sample (similar as to what would be measured by ELISA), indicates that a sample showing the average intensity of IL-2Rα expression corresponds to the number of metastatic foci found in the liver. For example, the sample of melanoma cells having the highest intensity of IL-2Rα expression, cells exposed to ConA, was also the sample of cells that caused the highest number of metastatic foci (FIG. 2, circle D).

1.2 Clinical applications of the measurement of the cell-associated expression of IL-2Rα by non-lymphoid tumors.

A. Determining a metastasis prognosis

Because of the problems that metastases present, in terms of diagnosis and treatment of non-lymphoid tumors, a method for determining a metastasis prognosis is desirable. One embodiment for determining the metastasis prognosis comprises the following steps: (a) Obtain samples of the primary tumor (presurgical or intrasurgical biopsy);

(b) Establish the percent of non-lymphoid cells with IL-2Rα by using any one of the methods, or a combination thereof, described above in 1.1 Sections A–E. The non-lymphoid tumor biopsy, and the tumor type, would influence the selection of the method best suited for determining the cell-associated expression of IL-2Rα in that specimen. For example, a clinical diagnostic kit comprising reagents for performing fluorescence microscopy may be best suited for determining IL-2Rα cell-associated expression in histological sections of frozen non-lymphoid tumor tissues, or for histological sections of fixed and embedded tumor tissues. A clinical diagnostic kit for determining IL-2Rα cell-associated expression in isolated non-lymphoid tumor tissue cells can comprise reagents and a microtiter plate for an ELISA; reagents and reaction vessels for a radioimmunoassay; reagents for FACS analysis; or reagents, including specific primers and probes, for PCR™ analysis. A clinical diagnostic kit essentially contains two basic elements: (1). An anti-IL-2Rα antibody coupled to a reporter compound such as a fluorochrome, chromophore, or enzyme. Examples of such compounds include alkaline phosphatase, fluorescein-5-isothiocyanate, peroxidase, phycoerythrin, and rhodamine; (2). An antibody against a tumor cell marker (TCM) known to those skilled in the art to be associated with the specific tumor type. Antibodies, against tumor cell markers associated with specific tumor types, which may be used in accordance with the method of the present invention include but are not limited to those listed in Table 2, infra.

TABLE 2

| ANTI-TCM ANTIBODY | SPECIFIC TUMOR TYPE |
| --- | --- |
| HEA125 MAb, HT29-15 MAb or B72.3 MAb | colorectal carcinoma |
| BCD-B4 MAb or NCRC-11 MAb | breast carcinoma |
| anti-PSA antibody or PD41 MAb | prostate carcinoma |
| ALT-04 MAb | lung carcinoma |
| B72.3 MAb, HMD4 MAb or COC183B2 | ovarian carcinoma |
| HEA-125 MAb, MM46 MAb, or 9.2.27 MAb | melanomas |
| MGb 2 MAb, or ZCE 025 MAb | gastric carcinoma |
| BW494 MAb | pancreatic carcinoma |
| CEB9 MAb | uterine cervical carcinoma |
| HSAN 1.2 MAb | neuroblastoma |
| HISL-19 MAb | neuroendocrinomas |
| TRA-1-60 MAb | seminoma |

MAb - monoclonal antibody

The anti-TCM antibody is coupled with a fluorochrome, chromophore, or enzyme differentiated from the one coupled to the anti-IL-2Rα antibody.

To determine the metastatis probability, two percentages are determined for the non-lymphoid tumor. The first percentage is calculated by measuring the percent of the tumor cells or percentage of tumor tissue surface, showing both antigens (IL-2Rα$^+$,TCM$^+$cells). The second percentage is calculated by counting the percentage of tumor cells which are identifiable by phenotype (including size, shape traits, flow cytometry forward angle light scatter (FALS)) and which are IL-2Rα positive (Tumor cell phenotype$^+$, IL-2Rα$^+$). The addition of both percentages is the coefficient of metastatic colonies forming cells (Met-CFC coefficient). The Met-CFC coefficient is proportional to the metastatic probability. Experimentally estimated as follows:

| Met-CFC coefficient | Metastasis Probability |
| --- | --- |
| 0% | 0% |
| <10% | <30% |
| >45% | 100% |

Note that IL-2Rα expression itself can be used experimentally to determine metastasis because T-cells are excluded in the purified tumor. However, in order to exclude T-cell IL-2Rα expression from a tumor biopsy, anti-TCM and tumor phenotype are used concurrently with IL-2Rα.

To illustrate this embodiment, and based on IL-2Rα expression alone, B16F10 melanoma cells were treated under different conditions to contrast metastasis efficiency with IL-2Rα expression. B16F10 cells pretreated in vitro as described above in Section F, except that the pretreatments consisted of incubating a different group of cells in of the following solutions: A) for 24 hours in regular growth media (control); B) for 24 hours in media containing 125 U/ml Il-2 (activates growth of metastatic cells); C) for 24 hours in media containing 10 U/ml IL-4 (blocks expression of IL-2Rα); D) 24 hours in media containing 5 μg/ml ConA (activates cell growth); or E) detaching the cells by brief exposure to 0.1% trypsin plus 2mM EDTA, then incubation of the cells for 48 hours in spinner flasks in DMEM plus 10% FBS (enhances cell growth). FACS analysis for IL-2 expression, and in vivo tumor cell growth and metastasis efficiency analysis were performed as described above in Section F except that each group of mice consisted of 6 members rather than 20. The results, shown in Table 3, indicate that where less than 10% of the cells express IL-2Rα, metastasis occurred in approximately 30% of the mice (B16F10, untreated; and IL-2 treated cells); where no cells express IL-2Rα, metastases did not occur in any of the mice (0% mice, cells treated with IL-4); where 35% of the cells express IL-2Rα, metastasis occurred in greater than 80% of mice (B16F10 grown in suspension); and where greater than 50% of the cells express IL-2Rα, metastasis occurred in 100% of the mice (B16F10 treated with ConA).

TABLE 3

| Pretreatment | Surface IL-2Rα % of cells | # of mice with metastasis |
| --- | --- | --- |
| B16F10 (untreated) | 7.4 ± 5.7 | 2/6 |
| B16F10 + IL-4 | 0 | 0/6 |
| B16F10 + IL-2 | 9.8 ± 6.3 | 2/6 |
| B16F10 + ConA | 59.5 ± 4.8 | 6/6 |
| B16F10 in suspension | 35.4 ± 2.2 | 5/6 |

Also high coefficients were found to be related with a preference for, or even exclusive metastatis for, what is termed herein as "prometastatic territories."

2. Treatment with anticancer therapy localizing to prometastatic territories, comprising targeted compounds directed to metastatic colonies forming cells and to dormant metastatic tumor cells, and monitoring the effect of that treatment.

2.1 Prometastatic territories.

Haematological malignancies, including leukemias and lymphomas, have been effectively treated by IL-2 fusion toxins which selectively bind and intoxicate cells bearing high affinity IL-2 receptors (LeMaistre et al., 1992, Immunol-Res., 11, 42–53; and Waldmann et al., 1992, Ann Intern Med. 116: 148–160); and by humanized antibodies to high affinity IL-2 receptors (hIL-2R), or anti-hIL-2R linked with toxins or radionuclides (Waldmann et al., 1992, supra). The method of the present invention for treating metastases of solid non-lymphoid tumors, and solid non-lymphoid tumors having a high probability of metastasis, differs in several important respects. The haematological malignancies express hIL-2R (comprised of both α and β chains) which is efficiently bound by IL-2 and anti-hIL-2R. Further, by the nature of the malignancy, treatment with the IL-2-toxin or anti-hIL-2R-toxin or anti-hIL-2R, comprises infusion systemically. Since the present invention shows a correlation between metastatic potential of a solid non-lymphoid tumor with expression of IL-2Rα, such non-lymphoid tumors expressing IL-2Rα have low affinity binding for IL-2-toxin or anti-hIL-2-Rotoxin or anti-hIL-2R. Thus, one method of the present invention for anticancer therapy against metastases of solid non-lymphoid tumors, and solid non-lymphoid tumors having a high probability of metastasis, comprises administering a therapeutically effective amount of a molecule linked to a toxic, radionuclide, or chemotherapeutic agent wherein the molecule is specific for (i.e. has high affinity binding to) IL-2Rα, such as humanized anti-IL-2Rα antibody.

Despite IL-2Rα's low affinity for IL-2, a relatively small dose of IL-2 concentrated in the prometastatic territories will activate resting metastatic tumor cells which makes them more susceptible to antineoplastic drugs. Thus according to the present invention, another method for treating metastatic colony forming cells and dormant metastatic cells comprises simultaneous delivery of IL-2 and antineoplastic drug to the prometastatic territories. Note that the methods of anticancer therapy according to this embodiment of the present invention do not comprise systemic administration, but rather comprise targeting the therapy directly to prometastatic territories.

The prometastatic territories, targeted by the anticancer therapy of the present invention, are identified by their vasculature, by the terminal sugar concentration, and concentration of extracellular adhesion molecules (ICAMs) expressed on the surface of the cells contained within the territory. Metastatic cells of solid non-lymphoid tumors only develop metastatic foci ("colonize") in a predictable location comprising unique capillary zones of the target organs such as liver and lung (Barberé-Guillem et al., 1989, Cancer Research 49:4003–4010; Barberé-Guillem et al., 1992, Int. J. Cancer Res. 52:974–977; Barberé-Guillem et al., 1993, Int. J. Cancer 53:298–301; Barberé-Guillem et al., 1993, Int. J. Cancer 54:880–884). For example, in liver, the prometastatic territories are located in the 1st half (primarily in the second quadrant of that half) of the sinusolds extending from the portal vein to the hepatic vein. This area of the sinusolds is also known as the periportal segment of the sinusolds. In the lung, the prometastatic territories are in the terminal pre alveolar venules and the pleural terminal capillaries. Similar regions have been demonstrated in other organs including the adrenal gland.

Figure 4:
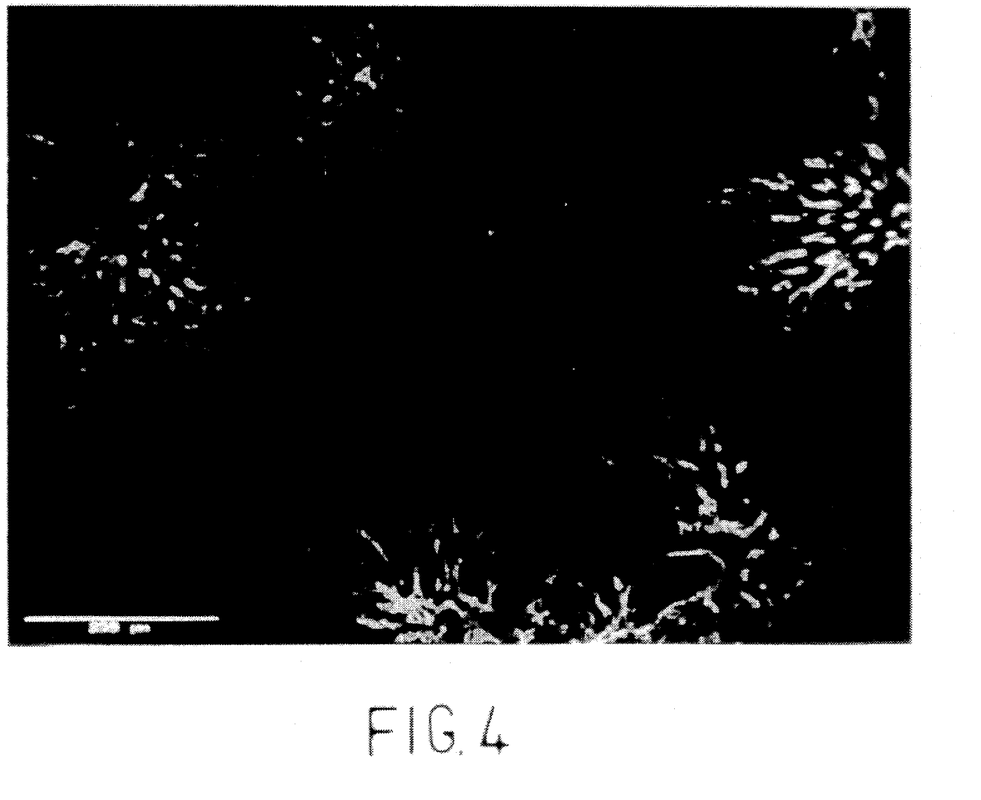
FIG. 4 is a photograph of a liver section showing the binding specificity of wheat germ agglutinin, tagged with rhodamine, for type 1 endothelial cells in the prometastatic territories (bright zones) versus the rest of the liver structure (dark areas).

The common factor of all characterized prometastatic territories is that the capillaries within the territory contain a specific subpopulation of endothelial cells termed "type 1 endothelial cells" (Vidal-Vanachlocha et al., 1993, Hepatology 18:328–339). Type 1 endothelial cells display an identifying characteristic on their cell surface comprising oligosaccharides having a high concentration of specific terminal sugars (N-acetyl galactosamine; Gal NAC), which is between 6 and 10 times higher than in the rest of the capillary zones (Barberé-Guillem et al., 1991, Hepatology 14:131–139; Vidal-Vanachlocha et al., 1993, supra). The higher expression of these specific sugars results in preferential binding to type 1 endothelial cells by lectins that join specifically to those sugars when the lectin is injected in a circulatory site just prior to the prometastatic territory. Thus, the injected lectins, such as wheat germ agglutinin (WGA), are arrested, and practically abducted in the prometastatic territories. This is shown in FIG. 4, wherein the liver zone where tumor cells do not colonize and develop, is free of WGA tagged with rhodamine (dark areas); and the capillary type 1 endothelial cells comprising the prometastatic territories are bound by WGA tagged with rhodamine (bright zones). Thus, the abduction of the lectin-fluorescent molecules occurs in the target area of the liver where tumor cells colonize and develop metastasis. The higher concentration of lectin contained in the capillaries comprising the prometastatic territories reflects the higher terminal sugar (Gal NAC) concentration of capillary type 1 endothelial cells in these territories.

The endothelial cells of the liver in the prometastatic territories also contain a higher concentration of ICAMs. Thus, a ligand or antibody with binding specificity for the ICAM can be used as a targeting agent specific for this cell subpopulation. Lung prometastatic territories also comprise endothelial cells containing a higher concentration of ICAMs (Zhu et al., 1993, Int. J. Cancer 53:628–633; Zhu et al., 1992, J. Clin. Invest. 89:1718–1724), and ligand or antibody with binding specificity for the ICAM can be used as a targeting agent specific for this cell subpopulation.

Figure 5A:
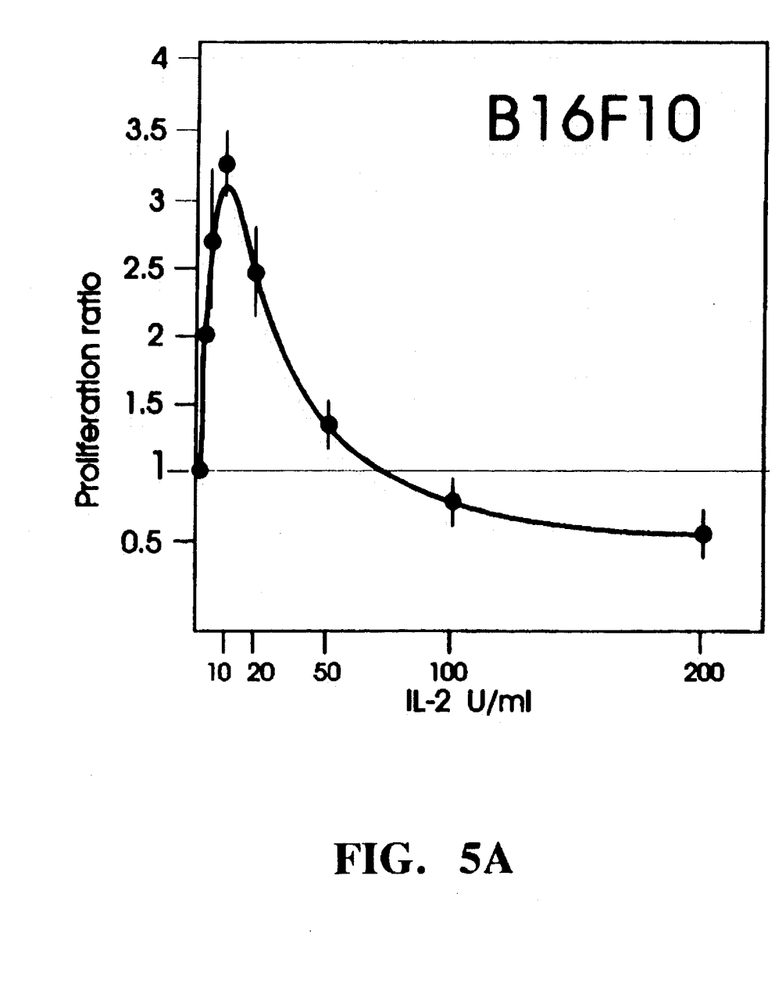
FIGS. 5A and 5B represent cell growth response to IL-2
Figure 5B:
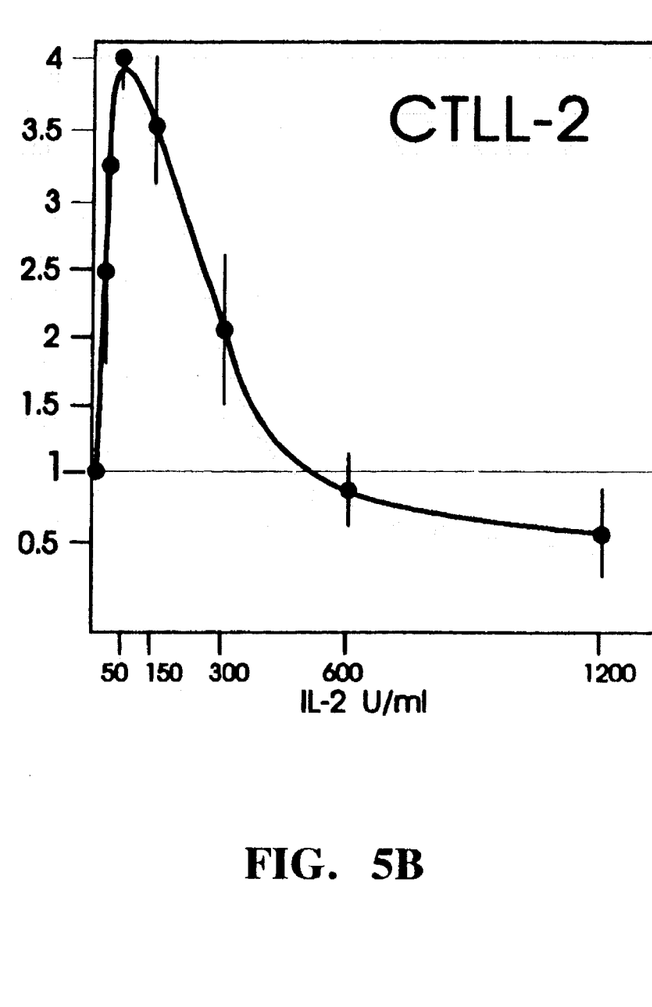

The metastatic cells arrested in the prometastatic territories can go into a dormant state or to a slow proliferative state (pseudo-resting) that is highly resistant to NK cells and to the antitumor drugs. They come out of this state under the influence of low local concentrations of IL-2 and IL-1. When the proliferation of blastic metastatic cell triggers off, they become more sensitive to antineoplastic drugs and to NK cells. As an illustration of the correlation of cytokine concentration and the resultant effects on non-lymphoid tumor cells growth, B16F10 melanoma cells were exposed to different concentrations of Il-L and IL-2, and the resulting growth response was noted. For the measurement of IL-2 effect on B16F10 melanoma cell growth, $10^4$ viable cancer cells were added to each well of a 96 well plate and the cultures were incubated at 5%$CO_2$ for 48 hours in serum-free or 10% FBS supplemented regular media containing a concentration of mouse recombinant IL-2 ranging from 10–200 U/ml; or 20, 125, or 250 U human recombinant IL-2 (hrIL-2). Then each well was pulsed with 1μCi [$^3$H]-thymidine, and harvested after 6 hours wherein the radioactivity was subsequently measured. The protocol for the measurement of IL-1 effect on B16F10 melanoma cell growth, $10^4$ viable cancer cells were added to each well of a 96 well plate and the cultures were incubated at 5%$CO_2$ for 48 hours in serum-free or 10% FBS supplemented regular media containing either 1, 10 or 20 U/ml mouse IL-1S. In some cases, anti IL-2Rα antibody was added simultaneously with the IL-1β. Each well was pulsed with 182 Ci of [3H]-thymidine, and harvested after 6 hours wherein the radioactivity was subsequently measured. FIG. 5 shows that high concentrations (greater than 75 U/ml) of IL-2 induces death or blastic cell cytostatis but does not affect the B16F10 metastatic cells in pseudo-resting state. Of therapeutic importance, note that IL-2 concentrations greater than 75 U/ml have a suppressing effect on cell growth of metastatic cells, and that that concentrations of between 75 U/ml and 100 U/ml are not toxic for lymphocytes (FIG. 5, represented by CTLL-2) prepared in a similar manner. Table 4 shows that IL-2 and IL-1 in low concentrations induces the step from pseudo-resting to blastic and induces the blastic cells proliferation.

TABLE 4

| Cytokine/concentration | B16F10 Response (mean, cpm) |
| --- | --- |
| Control | 60.12 ± 28.5 |
| anti-IL-2Rα antibody | 40.60 ± 7.9 |
| Mouse IL-2 (10 U/ml) | 2057.40 ± 540.7 |
| Mouse IL-2 (20 U/ml) | 3619.60 ± 116.2 |
| IL-1 (1 U/ml) | 61.85 ± 20.5 |
| IL-1 (10 U/ml) | 1083.30 ± 70.5 |
| IL-1 (20 U/ml) | 2045.60 ± 448.2 |
| IL-1 (10 U/ml) + anti-IL-2Rα antibody (1 μg/ml) | 571.19 ± 78.2 |
| IL-1 (10 U/ml) + anti-IL-2Rα antibody (4 μg/ml) | 98.64 ± 16.8 |
| FCS (10%) Control | 1594.30 ± 301.3 |
| anti-IL-2Rα antibody (4 μg/ml) | 565.40 ± 66.9 |
| Mouse IL-2 (20 U/ml) | 2556.60 ± 566.2 |
| FCS (10%) Control | 2135.32 ± 245.5 |
| hrIL-2 (20 U/ml) | 2012.52 ± 347.2 |
| hrIL-2 (125 U/ml) | 2452.22 ± 298.3 |
| hrIL-2 (250 U/ml) | 3181.62 ± 231.6 |

Thus, the methods of the present invention for treatment of metastases of solid non-lymphoid tumor, comprise anticancer therapy targeted to prometastatic territories. The advantages of such a method include that the anticancer therapy is directly targeted to cells in the prometastatic territories in the specific organ, thereby achieving therapeutic concentrations of antineoplastic drug or toxic agent in the area where metastases of solid non-lymphoid tumor cells are localized, with minimal harm to the immune and the hematopoietic systems.

2.2 Anticancer therapy directed to the prometastatic territories.

Specifically, the anticancer therapy according to the present invention comprises one or more of the following embodiments:

Embodiment (A). A compound comprising a therapeutically effective amount of IL-2 or IL-1, and antineoplastic drug (chemotherapeutic agent) is directed to the prometastatic territories to avoid the IL-2 cytostatic effect on the blastic cancer cells and to activate the pseudo-resting metastatic cells to avoid their resistance and to provide adequate concentration and uptake of antineoplastic drug to effect metastatic cell death.

In this embodiment, the IL-1 or IL-2 may be linked to a lectin molecule, and the antineoplastic drug may be linked to a lectin molecule, such as WGA, using methods known to those skilled in the art (as exemplified by allowed patent to Dr. Howard J. Allen), and those components mixed in a therapeutically effective ratio to provide a compound with higher affinity to the prometastatic territories which are the target of the anticancer therapy. Alternatively, an anti-ICAM antibody may be linked to the IL-1 or IL-2, and the same antibody linked to the antineoplastic drug, and those components are mixed in a therapeutically effective ratio to provide a compound with higher affinity to the prometastatic territories. Such compounds may be incorporated into carrier liposomes, using methods known to those skilled in the art, to increase retention time of the compound at the prometastatic territories. To investigate this embodiment, liposomes have been constructed which contain rhodamine inside and with incorporated WGA at the surface. Injection of these liposomes into the portal vein of the liver resulted in the same distribution of fluorescence as depicted in FIG. 4. In addition it was noted that the type 1 endothelial cells did not internalize the lectin-liposomes, leaving them exposed to the adjacent metastatic cells. However, a possible limitation is that it appears by the fluoresecence analysis, that Kupffer cells phagocytosed a small portion of the lectin-liposome composition.

Embodiment (B). A compound comprising a therapeutically effective amount of a molecule linked to a toxin, radionuclide, or chemotherapeutic agent wherein the molecule is specific for IL-2Rα, such as humanized anti-IL-2Rα antibody, is administered to the prometastatic zone to bind to the metastatic cells harbored therein to effect metastatic cell death.

In both Embodiments (A) and (B), the compound is administered through a catheter so as to introduce the compound directly into the vascular access of the prometastatic territories. Also, in both embodiments, the efficacy of treatment may be monitored by measuring the cell-associated expression of IL-2Rα by using any one of the methods, or a combination thereof, described above in 1.1 Sections A–E, wherein a decrease in the number of metastatic cells of non-lymphoid tumor expressing cell-associated IL-2Rα relative to the number of metastatic cells expressing cell-associated IL-2Rα prior to the initiation of treatment is indicative of an anticancer effect from therapy.

3. Treatment with anticancer therapy directed to non-lymphoid tumor cells expressing TCRβ, or tumoral-specific β chain variants.

3.1 The relation between TCRβ expression and non-lymphoid tumors.

In this embodiment of the present invention, anticancer therapy of non-lymphoid tumors, relies on the expression by these tumors of the T-cell receptor β (TCRβ) and/or β chain variants. Essentially, tumor cells may express several variable regions of the β chain of the TCR (mostly Vβ8), which display a hypervariable region candidate to express a tissular and/or tumoral specificity. Nevertheless, because its functional resemblance with lymphocyte TCR, these sequences, even being specific to the tissue, cannot be immunogenic.

Moreover, they can behave like inductor elements of the immunosuppression or of anergy. Thus, a method according to the present invention is to target anticancer therapy to non-lymphoid tumor cells expressing TCRβ.

In one embodiment of the present invention, the cell-associated expression of TCRβ was measured on solid, non-lymphoid tumors. The experiments showed that human and experimental non-lymphoid tumors express TCRβ. The following examples in Sections A through D demonstrate the detection of cell-associated TCRβ in human and experimental tumors using one or more methods selected from the group consisting of fluorescence microscopy (measuring surface TCRβ), mRNA Northern and slot blot analysis (measuring TCRβ m-RNA expression), enzymatic amplification and analysis of mRNA (measuring TCRβ m-RNA expression), and quantitative fluorescence analysis (measuring surface TCRβ) analysis. The human and experimental tumors were obtained as follows: B16P10 melanoma cells were supplied by Dr. MP Poupon (Paris). Colon 51B and colon 51 B lim 10 cells were supplied by Dr. R. Bresalier (USA). MCA-26 cells were supplied by Dr. I. Fidler (USA). MMC-7489 and cells were supplied by Dr. J. Vaageand (USA). SW480, SW480E, SW480R and SW620 were supplied by Dr. I. B. Weinstein. Human biopsies were supplied by Dr. Alonso and Dr. Pellin (Spain). Other tumor cell lines were obtained from the ATCC. All tumor cell lines were grown in plastic T-flasks in a humid atmosphere of 5% $CO_2$ in air, in adequate media supplemented with 10% FBS and containing penicillin and streptomycin. In order to eliminate possible lymphocyte contamination of human tumor cell samples the specimens were prepared as follows. Samples of tumors were removed from the patient under surgical conditions; washed in medium containing penicillin and streptomycin; and minced and stirred in 20 ml GBSS containing 0.02% PronaseE (Sigma, USA) and 0.05% Type I Collagenase at 37° C. for 10 minutes at a pH of 7.4. The cell suspensions were then filtered through nylon gauze and centrifuged twice at 250×g for 10 minutes. The isolated cells were then implanted subcutaneously in nude mice. After 21 days of tumor growth, the tumor cells were sampled for investigations of TCRβ expression.

A. Fluorescence microscopy of TCRβ Tumor biopsies or surgical specimens containing non-lymphoid tumor may be disaggregated, and prepared directly for fluorescence analysis. Alternately, the tumor cells can be cultured in 8-well slide plates (Biotek) for 48 hours, then the supernatants removed and the wells washed gently with PBS and fixed in Carnoy's fixative. After three PBS rinses, the cells were incubated for 30 minutes at 37° C. in a solution of PBS containing 4 μl/ml FITC-rat anti-human-TCRB (constant and variable regions) monoclonal antibodies (Genzyme, Boehringer Manheim). After incubation, the wells were washed twice with PBS. Controls were prepared only with FITC rat anti-mouse-$IgG_2$ monoclonal antibody (Boehringer Manheim). The cells were observed with a laser-scanning fluorescence microscope.

B. mRNA Northern and slot-blot analysis mRNA was obtained from spleen cells, ConA-activated spleen cells, and tumor cells. After extraction and quantification of the mRNA (shown to be intact by 0.7% agarose gel electrophoresis), a total of 20 μg of purified RNA was separated on a 1.2% agarose gel containing 2.2 M formaldehyde. The electrophoresis was performed at 80 V. The tracks containing the molecular size standard was cut off the gels and the migration distances were measured. The gels were rinsed and transferred onto nitro-cellulose filter. Two μg of mRNA were diluted in a final volume of 100 μl in 10×SSC-formaldehyde and denatured by heating at 65° C. for 10 minutes before blotting. mRNA was cross-linked to the nitrocellulose filter with UV irradiation. The blots were prehybridized 4 hours at 45° C. in 6×SSC, 0.5 SDS, 5×Denhardt's, 10 mM EDTA, 50 μg/ml of sheared salmon sperm DNA, and 50 μg/ml of E. coli tRNA. Simultaneously 5 picomoles of DNA probe, to murine or human TCRβ (Clontech), were labeled according to standard protocol by 5'end-labeling of oligonucleotide probe with gamma-$^{32}$P ATP. 100 μg of human beta-actin DNA probe (Clontech) was labeled by random priming. The radiolabeled probes ($2\times10^9$ cpm/μl specific radioactivity) were used for hybridization of mRNA blot at 45° C. for 24 hours. Then the blots were washed with 5×SSC-0.1 SDS at the hybridization temperature for 20 minutes. The blots were exposed to x-ray film with intensifying screens at −70° C. for various periods. The probes were removed from the filters by incubation in sterile water at 100° C. for 10 minutes and the filters were rehybridized with other probes. Quantitative analysis of 10 autoradiograms were performed with video-densitometry.

C. Enzymatic amplification of tumor cell mRNA

Expression of TCRβ mRNA can be detected by extracting and purifying mRNA from non-lymphoid tumor cells and then subjecting the purified mRNA to enzymatic amplification to obtain sufficient quantities for analysis and detection. Enzymatic amplification techniques which could be employed include those known in the art such as PCR™ (polymerase chain reaction), QB replicase, and NASBA (nucleic acid sequence-based amplification). Detection of the amplified nucleic acid includes techniques known in the art including, but not limited to, agarose gel electrophoresis and Northern blotting; fluorescence-based hybridization assays; chemiluminescence-based hybridization assays, and capture hybridization microtiter assays. Oligonucleotides primers and probes can be synthesized from the nucleic acid sequence of the TCRβ gene as evidenced in the art (Waters et al., 1992, Diabetes 41:308–312). Probes can be synthesized with methods known to those skilled in the art to incorporate either non-isotopic or isotopic label. Alternatively, the label may be incorporated directly into the amplified product.

In this example, single-stranded cDNA, obtained by reverse transcription from the extracted tumor cell mRNA, was amplified by PCR™ utilizing primers for TCRβ genes from commercial sources. The amplified products were separated on a 1.2% agarose gels and stained with ethidium bromide in parallel with positive and negative controls. Quantification was made with Photoquant System™ (BAF, Spain).

D. Quantitative fluorescence analysis

Tumor cells were cultured in 24-wells plates for 48 hours, and then the supernatants were removed and the wells washed gently with PBS, then the cells were gently scraped from tissue culture plates and incubated in a solution of PBS containing 1 μg/ml rat FITC conjugated anti-mouse-TCRβ monoclonal antibody for 30 minutes at 4° C., then fixed with 1% paraformaldehyde, and analyzed within 48 hours using a microfluorimeter. In all cases, controls were prepared with second antibody alone. Spleen cells were used as negative control and ConA-activated spleen cells as positive control of antigen expression. Quantitative analysis of TCRS expression on tumor cells was performed using special software (ImageI, USA; and Photoquant, Spain).

Table 5 shows that cell-associated expression of TCRS correlates well with human nonolymphoid tumors.

TABLE 5

TCRβ Expression on Human Non-Lymphoid Tumor Cells

| Tumor | Type of Tumor | TCRβ mRNA |
|---|---|---|
| *Established Tumor Cell Lines* | | |
| LS174T | colonic carcinoma | + |
| T84 | colonic carcinoma | + |
| SW620 | colonic carcinoma | + |
| SW480 | colonic carcinoma | + |
| R2 | colonic carcinoma | + |
| E8 | colonic carcinoma | + |
| A549 | lung carcinoma | − |
| SEPPLO | renal carcinoma | − |
| HELA | cervix carcinoma | − |
| HL-60 | promyelocytic leukemia | + |
| HepG2 | hepatoma | − |
| *Primary Tumor Biopsies* | | |
| BVal50 | osteosarcoma | − |
| BVal21 | osteosarcoma | + |
| BVal84 | osteosarcoma | + |
| BVal8 | osteosarcoma | + |
| BVal46 | osteosarcoma | + |
| BVal76 | osteosarcoma | − |
| BVal102 | osteosarcoma | + |
| BVal56 | osteosarcoma | + |
| BVal88 | osteosarcoma | + |
| BVal100 | osteosarcoma | + |
| BVal154 | osteosarcoma | + |
| BVal-C1594 | rethinoblastoma | + |
| BVal-C-700 | rethinoblastoma | + |
| BVal611 | osteosarcoma | − |

3.2 Clinical applications of the cell-associated expression of TCRβ by human solid non-lymphoid tumors 3.2.1 Immune modulation The present invention provides methods for targeting compounds, via TCRβ specificity, directed to metastatic colony forming cells and to dormant metastatic tumor cells. The Staphylococcal Enterotoxins (SEA, SEB, etc.) link TCR variable β chains of tumor cells to CMH II of antigen presenting cells, and consequently a comodulation of immune system and of tumor cells is produced. These reactions are related with the absence of immune response against most of the tumors and with the tumor cells passing to a reserve state capable of being reverted under casual inflammatory circumstances, even years later after the primary tumor eradication.

The TCRβ-targeted methods of the present invention, directed to colony former metastatic cells, dormant cells and cancer cells in general, involve immune modulation as described in the following embodiments:

Embodiment (A). A method of modulation of the immune response can be achieved by supplying molecules able to identify TCRβ-specific sequences of tumor cells of each specific origin (organ, tissue, cell group, etc.) and be recognized by the immune system cells, directing the desired immune process interactions. These molecules include the Staphylococcal enterotoxins or anti-TCRβ idiotype linked to IL-1 or Il-2.

Embodiment (B). A method of tumor proliferation modulation can be achieved by supplying molecules able to identify TCRS-specific sequences of tumor cells of each specific origin (organ, tissue, cell group, etc.) and be recognized by the immune system cells, directing the desired immune process interactions.

Immune modulation or tumor proliferation modulation can be achieved by producing anti-TCRβ idiotype monoclonal antibodies against non-lymphoid tumor cells of different groups, based on organ specificity of the tumor, for their diagnostic and pharmacological use. Alternatively, antibodies to soluble human TCRβ isolated from the specific nonolymphoid tumor can be made according to the method of Basi et al. (1992, *J. of Immunol. Methods* 155:175–191), wherein the antibodies generated recognize multiple epitopes on cell-surface TCR expressed by that non-lymphoid tumor. A compound comprising a therapeutically effective amount of IL-2 or IL-1 linked to the anti-TCRβ idiotype antibody, using methods known to those skilled in the art, to provide the compound with properties that may effect immune modulation. Such a compound may comprise IL-1 or IL-2 contained within carrier liposomes, and anti-TCRβ idiotype antibody incorporated into the surface of liposomes using methods known to those skilled in the art. The compound may be administered systemically.

3.2.2 TCRS-targeted antineoplastic drug therapy

Specifically, the TCRβ-targeted antineoplastic drug therapy, according to the present invention, comprises a compound comprising a therapeutically effective amount of a molecule linked to a toxic, radionuclide, or chemotherapeutic agent wherein the molecule is humanized anti-TCRβ idiotype antibody which is administered systemically. Such a compound may comprise chemotherapeutic agents contained within the carrier liposomes, and the anti-TCRβ idiotype antibody incorporated into the surface of the liposomes, using methods known to those skilled in the art. The efficacy of treatment may be monitored by measuring the cell-associated expression of TCRβ by using any one of the methods, or a combination thereof, described above in 3.1 Sections A–D, or by using clinical diagnostic kits comprising immunoassays with anti-TCRβ idiotype antibody, wherein a decrease in the number non-lymphoid tumor cells expressing cell-associated TCRβ relative to the number of non-lymphoid tumor cells expressing TCRβ prior to initiation of treatment is indicative of an anticancer effect from therapy.

Peptides corresponding to the anti-TCRβ idiotype of tumor cells can be incorporated to MHC II context of the APC for their pharmacologic use.

In targeting agents to bind to TCRβ, it may be necessary, because of tumoral specific variants of the β chain, to isolate tumor cells from the patient to raise specific anti-TCRβ idiotype antibody to the tumoral variant, or to determine the nucleic acid sequence of the variant to synthesize the corresponding peptides.

Although the present invention has been described in some detail by way of illustration and example for purposes of clarity and understanding, various modifications will become apparent to those skilled in the related arts from the foregoing description and figures. Such modifications are intended to be included within the spirit of this application and within the scope of the appended claims.

What is claimed is:

1. A method for determining the prognosis of metastatic potential of a solid non-lymphoid tumor, comprising the steps of:

(a) measuring cell-associated IL-2Rα, and differentially measuring a tumor cell marker specific for that tumor type from a sample of said tumor;

(b) calculating a first percentage comprising tumor cells or tumor tissue surface showing the presence of IL-2Rα and said tumor cell marker;

(c) calculating a second percentage comprising tumor cells identifiable by phenotype using one or more characteristics selected from the group consisting of size, shape traits, FALS, said tumors also showing the presence of IL-2Rα; and (d) adding the first percentage to the second percentage to obtain a metastatic colony forming cells (Met-CFC) coefficient, said coefficient being proportional to the prognosis of metastatic potential in the following relationship:

| Met—CFC coefficient | Metastatic Potential |
|---|---|
| 0% | 0% |
| <10% | <30% |
| >45% | 100%. |

2. The method of claim 1, wherein the cell-associated IL-2Rα is measured by a method selected from the group consisting of fluorescence microscopy, Western blot analysis, m-RNA Northern and slot blot analyses, enzymatic amplification and analysis of m-RNA, fluorescence activated cell sorting, and an immunoassay.

3. The method of claim 1, wherein the tumor cell marker specific for that tumor type is measured by the use of an antibody with binding-specificity for that tumor cell marker, said antibody is selected from the group consisting of HEA125 MAb, HT29-15 MAb, B72.3 MAb, BCD-B4 MAb, NCRC-11 MAb, anti-PSA antibody, PD41 MAb, ALT-04 MAb, HMD4 MAID, COC183B2 MAb, HEA-125 MAID, MM46 MAb, 9.2.27 MAID, MGb 2 MAb, ZCE 025 MAID, BW494 MAID, CEB9 MAID, HSAN 1.2 MAb, HISL-19 MAID, TRA-1-60 MAb.

4. A method for monitoring efficacy of anticancer therapy of metastases of solid non-lymphoid tumors directed to prometastatic territories of a target organ, said method comprising measuring the cell-associated IL-2Rα expressed by said metastases, wherein a decrease in the number of metastatic cells of non-lymphoid tumor expressing cell-associated IL-2Rα relative to the number of cells expressing cell-associated IL-2Rα found prior to treatment indicates an anticancer effect from therapy.

5. The method of claim 4, wherein the cell-associated IL-2Rα is measured by a method selected from the group consisting of fluorescence microscopy, Western blot analysis, m-RNA Northern and slot blot analyses, enzymatic amplification and analysis of m-RNA, fluorescence activated cell sorting, and an immunoassay.

6. A clinical diagnostic assay kit for aiding in the determination of the prognosis of metastatic potential of a solid non-lymphoid tumor, comprising reagents for measuring tumor cell-associated IL2Rα, and reagents for differentially measuring a tumor cell marker for that tumor type from a sample of said tumor, wherein the reagents used for measuring tumor cell-associated IL-2Rα consist essentially of anti-IL-2Rα antibody useful for a method of detection selected from the group consisting of fluorescence microscopy, Western blot analysis, fluorescence activated cell sorting, and an immunoassay.

7. The kit of claim 6, wherein the reagent for measuring the tumor cell marker specific for that tumor cell type comprises an antibody with binding-specificity for that tumor cell marker, said antibody is selected from the group consisting of HEA125 MAb, HT29-15 MAb, B72.3 MAb, BCD-B4 MAb, NCRC-11 MAb, anti-PSA antibody, PD41 MAb, ALT-04 MAID, HMD4 MAb, COC183B2 MAb, HEA-125 MAb, MM46 MAb, 9.2.27 MAb, MGb 2 MAID, ZCE 025 MAb, BW494 MAb, CEB9 MAb, HSAN 1.2 MAb, HISL-19 MAb, TRA-1-60 MAb, or a combination thereof.

8. A clinical diagnostic assay kit for aiding in monitoring the efficacy of anticancer therapy of metastatic cells of a solid non-lymphoid tumor, comprising reagents for measuring tumor cell-associated IL2Rα, and reagents for measuring a tumor cell-associated tumor specific TCRβ idiotype, wherein the reagents used for measuring tumor cell-associated IL-2Rα consist essentially of anti-IL-2Rα antibody useful for a method of detection selected from the group consisting of fluorescence microscopy, Western blot analysis, fluorescence activated cell sorting, and an immunoassay.

9. The kit of claim 8, wherein the reagents used for measuring cell-associated tumor specific TCRβ idiotype comprise TCRS idiotype-specific reagents consisting essentially of anti-TCRS idiotype antibody useful for a method of detection selected from the group consisting of fluorescence microscopy, quantitative fluorescence analysis, and an immunoassay; or TCRβ idiotype-specific oligonucleotides useful for a method of detection selected from the group consisting of m-RNA Northern and slot blot analyses, and enzymatic amplification and analysis of m-RNA.

10. A method of predicting the metastatic potential of a solid non-lymphoid tumor, comprising obtaining a sample of solid non-lymphoid tumor cells, and measuring the tumor cell-associated expression of IL-2Rα in said tumor cells, wherein the metastatic potential of the solid non-lymphoid tumor is predicted to be:

(a) 0%, when no tumor cells are detected as expressing IL-2Rα;

(b) approximately 30%, when between about 1% to about 10% of the tumor cells are detected as expressing IL-2Rα; and (c) greater than about 80%, when greater than about 35% of the tumor cells are detected as expressing IL-2Rα.

11. The method of claim 10, wherein the cell-associated IL-2Rα is measured by a method selected from the group consisting of fluorescence microscopy, Western blot analysis, m-RNA Northern blot and slot blot analyses, enzymatic amplification and analysis of m-RNA, fluorescence activated cell Sorting, and an immunoassay.

\* \* \* \* \*